United States Patent
Kontothanassis et al.

(10) Patent No.: US 7,761,140 B2
(45) Date of Patent: Jul. 20, 2010

(54) STATE-BASED LOAD SHEDDING FOR PHYSIOLOGICAL SIGNALS

(75) Inventors: Leonidas Kontothanassis, Arlington, MA (US); Amir Bar-or, Newton, MA (US); David Goddeau, Watertown, MA (US); Jean-Manuel Van Thong, Arlington, MA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 836 days.

(21) Appl. No.: 11/699,616

(22) Filed: Jan. 30, 2007

(65) Prior Publication Data

US 2008/0183050 A1 Jul. 31, 2008

(51) Int. Cl.
*A61B 5/00* (2006.01)

(52) U.S. Cl. .............. 600/509; 600/300; 600/481; 600/483; 600/485

(58) Field of Classification Search .............. 600/301, 600/481, 483, 485, 509
See application file for complete search history.

(56) References Cited

U.S. PATENT DOCUMENTS

| | | | |
|---|---|---|---|
| 5,464,431 A | 11/1995 | Adams et al. | |
| 5,998,386 A | 12/1999 | Feldman et al. | |
| 6,152,883 A * | 11/2000 | Blanchett et al. | 600/521 |
| 6,701,183 B2 | 3/2004 | Baker et al. | |
| 6,826,425 B2 | 11/2004 | Bardy | |
| 6,871,089 B2 | 3/2005 | Korzinov et al. | |
| 6,879,856 B2 | 4/2005 | Stadler et al. | |
| 6,904,801 B1 | 6/2005 | Bridges et al. | |
| 7,218,960 B1 * | 5/2007 | Min et al. | 600/509 |
| 2005/0165320 A1 | 7/2005 | Glass et al. | |

OTHER PUBLICATIONS

Moody, G.B. and R.G. Mark, "A New Method for Detecting Atrial Fibrillation Using R-R Intervals," *Computers in Cardiology* 1983, pp. 227-230.
Babcock, B. et al., "Load Shedding for Aggregation Queries Over Data Streams," *Proceedings 20th International Conference on Data Engineering*, Mar. 30, 2004-Apr. 2, 2004, pp. 350-361.
Abadi, D.J., "The Design of the Borealis Stream Processing Engine," *Proceedings of the 2005 CIDR Conference*, pp. 277-289.
Reiss, F. and J.M. Hellerstein, "Data Triage: An Adaptive Architecture for Load Shedding in TelegraphCQ," *Proceedings of the 21st International Conference on Data Engineering (ICDE 2005)*, (2 pp.).
Gedik, B. et al., "Adaptive Load Shedding for Windowed Stream Joins," Center for Experimental Research in Computer Systems, GIT-CERCS-05-05 (2005).
International Search Report for S.N. PCT/US2008/052423 dated Jan. 30, 2008 (3 pages).

* cited by examiner

*Primary Examiner*—Carl H Layno
*Assistant Examiner*—Deborah Malamud

(57) ABSTRACT

A method of load-shedding in a system having a plurality of signal sources is disclosed. The method comprises the steps of: (a) for each signal source $S_i$ selected from a set of sources $\{S_1, S_2, \ldots\}$, each source having state $p_{i,k}$ selected from a set of states $\{p_{1,1}, p_{1,2}, \ldots, p_{1,N}; p_{2,1}, p_{2,2}, \ldots, p_{2,N}; \ldots\}$, wherein i is an integer greater than one, N is an integer not less than two and k is an integer from 1 to N: (i) obtaining fractions $f_{i,k}$, wherein each $0 \leq f_{i,k} < 1$ is a fraction of a signal from source $S_i$ to be discarded if source $S_i$ is in state $p_{i,k}$; and (ii) determining respective state $p_{i,k}$ of signal source $S_i$ based on the signal from source $S_i$; and (b) for each source signal $S_i$ in determined state $p_{i,k}$, discarding fraction $f_{i,k}$ of a signal from source $S_i$.

25 Claims, 4 Drawing Sheets

STATE-BASED LOAD SHEDDING FOR PHYSIOLOGICAL SIGNALS

BACKGROUND

During continuous physiological monitoring, which can play a crucial role in finding and treating asymptomatic pathologies in patients, useful physiological data is collected and analyzed. Examples of collected data include electrocardiograms (EKG), blood oxygen levels, weight, blood pressure and many others.

In such a setting, patients wear collecting devices. Collecting devices transmit data to an aggregator when the devices are within transmission range. The aggregator, in turn, transmits the data to a remote archival and analysis platform. Care providers are given secure access to the back end system so they can monitor their patients, receive notifications and/or alerts, and possibly provide feedback to the patients based on the analysis and their own expertise.

When the system's or system components' capacity for handling and processing a stream of data is exceeded, load-shedding is triggered, whereby a portion of the signal is discarded without processing.

Existing systems that implement load-shedding techniques either assume a priori knowledge of the value of incoming data or revert to dropping data in a random manner. The assumption of a priori knowledge is hard to enforce in practice (especially in the medical domain), and random shedding is far from optimal for many analysis algorithms.

BRIEF DESCRIPTION OF THE DRAWINGS

Features and advantages of the present disclosure will become apparent by reference to the following detailed description and drawings, in which like reference numerals correspond to similar, though not necessarily identical components. For the sake of brevity, reference numerals or features having a previously described function may not necessarily be described in connection with other drawings in which they appear. The drawings are not necessarily to scale, emphasis instead being placed upon illustrating the principles of the invention.

DETAILED DESCRIPTION

Disclosed herein are a method and an apparatus for load-shedding that are based on determination of a state of a signal source, such as a pathological state of a patient in an embodiment where physiological signals are being monitored.

Accordingly, in one embodiment, the monitoring system collects signals from a plurality of sources $S_i$ selected from a set of sources $\{S_1, S_2, \ldots\}$. Each source $S_i$ has state $p_{i,k}$ assigned to it. Each state is selected from a set of states $\{p_{1,1}, p_{1,2}, \ldots, p_{1,N}; p_{2,1}, p_{2,2}, \ldots, p_{2,N}; \ldots\}$. As used herein, i denotes the ordinal number of a source and is an integer greater than one; N denotes the total number of states per each source and is an integer not less than two; and k denotes the ordinal number of a state of the i-th source and is an integer from 1 to N.

The load-shedding method implemented in such a system performs the steps of: obtaining (by receiving as an input or computing) fractions $f_{i,k}$, determining respective state $p_{i,k}$ of signal source $S_i$ based on the signal from source $S_i$; and, for each source signal $S_i$ in state $p_{i,k}$, discarding fraction $f_{i,k}$ of a signal from source $S_i$. Here, each $0 \leq f_{i,k} < 1$ is a fraction of a signal from source $S_i$ to be discarded if source $S_i$ is in state $p_{i,k}$.

The method disclosed herein has several advantages over prior approaches. Controlling data load allows the monitoring systems to be designed for processing the average, rather than the peak data streaming rate. As a consequence, power consumption for and total cost of the system are significantly reduced at little or no loss of the quality of monitoring. It is believed that no knowledge of the intrinsic value of the data is required for the operation of the method and the apparatus of the present disclosure. Furthermore, embodiments disclosed herein make it possible to maintain high quality of detection of such events as atrial fibrillation even under high load conditions by discarding data in a manner that least affects the detection algorithms.

I. Continuous Monitoring Systems

The discussion below focuses on a continuous monitoring system designed for monitoring physiological data. It is to be understood however, that the method and the apparatus described herein may be employed in any other system used for continuously collecting data and transmitting the collected data from a collecting device, to an aggregating device and further to a processing and storage device.

Figure 1:
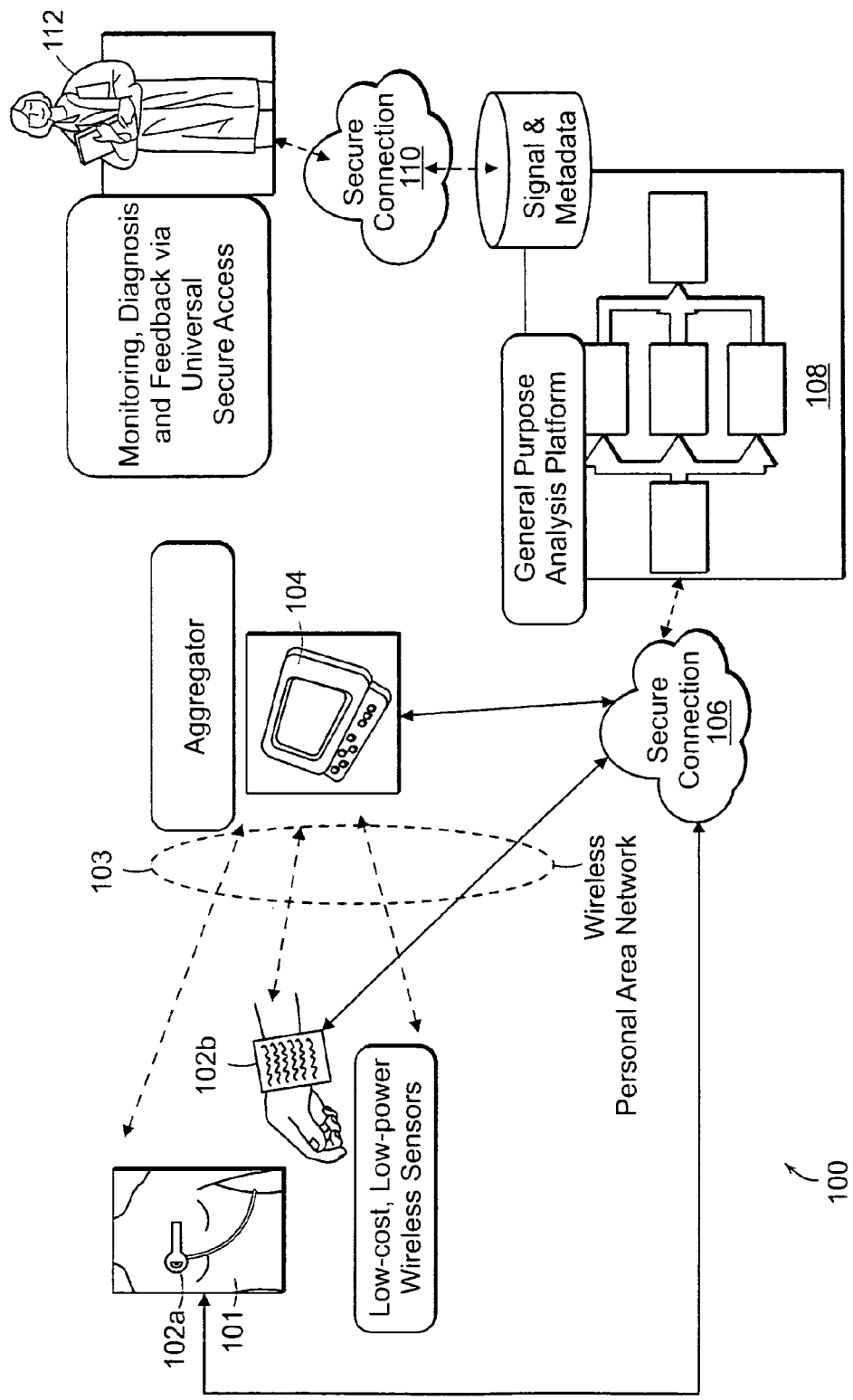
FIG. 1 is a schematic diagram of a continuous monitoring system employing an embodiment of the method and the apparatus disclosed herein.

An example of a continuous monitoring system that employs the method and the apparatus disclosed herein is shown in FIG. 1. Patients 101 wear data-collecting devices 102a or 102b that continuously collect physiological data of interest. The data is aggregated by aggregator 104 and transmitted via connection 106 to a remote analysis and archiving platform 108 for further archiving and analysis. Care providers 112 are given secure access to remote analysis and archiving platform 108 over connection 110 so they can monitor their patients 101, receive notifications and/or alerts, and possibly provide feedback to the patients based on the analysis and their own expertise.

Figure 2:
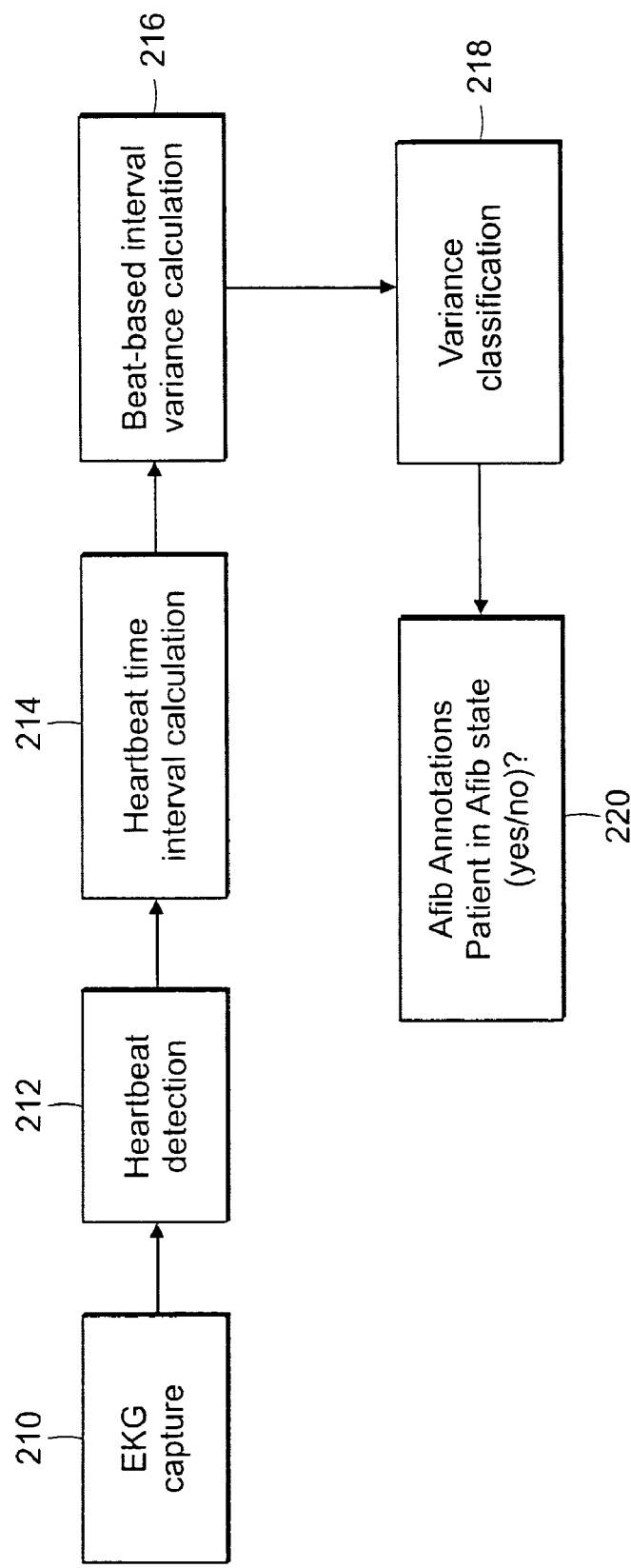
FIG. 2 is a flow-chart showing the steps of an embodiment of a method of detecting atrial fibrillation events.

FIG. 2 shows a flow chart that describes a typical analysis algorithm for detecting atrial fibrillation events (Afib) that may be implemented in analysis and archiving platform 108. At step 210, the patient's electrocardiogram (EKG) is captured. At step 212, heartbeats of the patient are detected by analyzing his EKG signal. At step 214, the time intervals between successive heartbeats (inter-beat intervals) are computed. At step 216, the variance of inter-beat intervals is computed. The variance of the inter-beat intervals is calculated either for a pre-determined time or for a pre-determined number of detected cardiac beats.

At step 218, the portions of the EKG signals that include high variance values are classified as atrial fibrillation events, while the portions that include low variance values are classified as normal sinus rhythm.

At step 220, the annotations are added to the EKG signal so that the portions of the EKG signals that include high variance values are classified as atrial fibrillation events, while low variance values are classified as normal sinus rhythm.

At step 220, a smoothing operation is applied to the output provided by the classification step 218 to reduce volatility in the output of the classifier 218. The smoothing procedure discards portions of the EKG signal classified as atrial fibrillation events if the duration of such portion falls below a pre-determined threshold value T. Threshold value T can be measured in units of time or in numbers of cardiac beats. (See G. B. Moody and R. Mark, "A new method for detecting atrial fibrillation using r-r intervals", *Computers in Cardiology* 1983, IEEE Computer Society Press (1983), pages 227-230 and U.S. Pat. Pub. No. 20050165320). Typically, the threshold number of beats is less than about 500 beats, less than about 400 beats or, preferably, about 300 or less. Alternatively, the threshold duration is less than about 15 minutes, less than about 10 minutes or, preferably, is 5 minutes or less.

Thus, atrial fibrillation is detected.

Methods of using inter-beat interval variance for detection of atrial fibrillation events is described, for example, in. Moody et al. and in U.S. Pat. Pub. No. 20050165320, cited above. The entire teachings of these publications are incorporated herein by reference. In short, an event is classified as atrial fibrillation if variance of inter-beat intervals, computed either over a pre-determined time or over a pre-determined number of beats, is above a threshold value V. Typically, V is 200 (in units of standard deviation).

Alternatively, an atrial fibrillation detection method that may be used with embodiments of the load-shedding disclosed herein is a method disclosed in the co-pending U.S. patent application Ser. No. 11/241,294, entitled "METHOD AND APPARATUS FOR IMPROVING THE ACCURACY OF ATRIAL FIBRILLATION DETECTION IN LOSSY DATA SYSTEMS", filed on Sep. 29, 2005. The entire teachings of this patent application are herein incorporated by reference.

II. Load-Shedding in Continuous Monitoring System

In an environment like the one depicted in FIG. 1, patients 101 are not expected to be within range of aggregator 104 at all times. As a consequence, devices 102a and 102b may be equipped with some amount of buffer memory for storing the collected signal when the device is not within transmission range. When devices 102a and 102b get back to within aggregator 104 transmission range, they will burst the already collected data to aggregator 104 which will, in turn, transmit such date to analysis and archiving platform 108 for analysis. In one embodiment, devices 102a and 102b transmit data across a wireless network 103 or the like to aggregator 104. Other networks 103 are suitable.

This bursty behavior may, in some instances, create a problem for the design of analysis and archiving platform 108. One can design platform 108 to handle the sum of the peak data rates of all devices such as 102a and 102b, or one can design platform 108 to handle the sum of the average data rate of all devices. Designing platform 108 for peak data rates may be more than an order of magnitude more expensive than designing platform 108 for an average data rate. Therefore, the peak data rate design may be undesirable, especially when chronic, non-acute pathologies are being monitored. For such pathologies, a system that is able to shed load while maintaining a high quality of pathology detection may be more desirable.

Load-shedding methods of data processing involve discarding some data without processing. Load-shedding is described, for example, in Reiss et al., "Data Triage: An Adaptive Architecture for Load Shedding in TelegraphCQ", Proceedings of the International Conference of Data Engineers (ICDE) 2005, pages 155-156; Babcock et al., "Load Shedding for Aggregation Queries over Data Streams", Proceedings of the 20th International Conference on Data Engineering (ICDE) 2004, page 350; and Abadi et al., "The Design of the Borealis Stream Processing Engine", CIDR (2005), pages 277-289. The entire teachings of these publications are incorporated herein by reference.

Prior methods of load-shedding discard data under the assumption that the information content of that data is of little or no interest with respect to extracting useful information from the signal. However, deciding which portions of the signal can be discarded without affecting the quality of detection is extremely difficult.

Disclosed herein is a method of load-shedding that does not require a priori knowledge of the data or any assumption about the informational content of the discarded data. In one embodiment, for example, the load shedding method of the present disclosure is employed in a cardiac monitoring system that detects atrial fibrillation events (Afib). In this embodiment, analysis and archiving platform 108 detects the state of each patient ("normal" or "pathological"), for example, using the method of FIG. 2, and issues load-shedding directives (load-shedding policy).

It is to be understood, however, that the method described below may be applied in other settings. In particular, the number of states of each signal source (such as normal or pathological state of each patient being monitored) may be any suitable number, and is not limited to two.

Load shedding may be applied to every stream (i.e., a stream from collecting devices 102a and 102b to aggregator 104, or a stream from aggregator 104 to analysis and archiving platform 108, or any other data stream of the system shown in FIG. 1 or of any other system not described herein), or a subset of the streams. Preferably, an embodiment of the system employs a load-shedding policy-issuing method described in co-pending U.S. patent application Ser. No., entitled "METHOD AND SYSTEM FOR SHEDDING LOAD IN PHYSIOLOGICAL SIGNALS PROCESSING", filed on Jan. 30, 2007. The entire teachings of this application are incorporated herein by reference.

III. Embodiments of Load-Shedding Methods

In one embodiment, the method of the present disclosure is based on the fact that physiological conditions ("normal" or "pathologic" states) of patient having chronic conditions or disorders do not change rapidly and tend to persist over time. Therefore, even if the exact onset of a pathological state is missed, the time period during which that patient's state is pathological will be captured correctly. One skilled in the art will readily appreciate, however, that the method described below may be applied in other settings.

A description of one embodiment of the method will now be given with reference to FIG. 3. In this embodiment, each signal source S has two states $p_1$ and $p_2$. For example, state $p_1$ may correspond to a "normal" state and state $p_2$ may correspond to a "pathologic" state. The signal sources S can be, for example, data collecting devices 102a and 102b collecting data from patients 101 (see FIG. 1).

Figure 3:
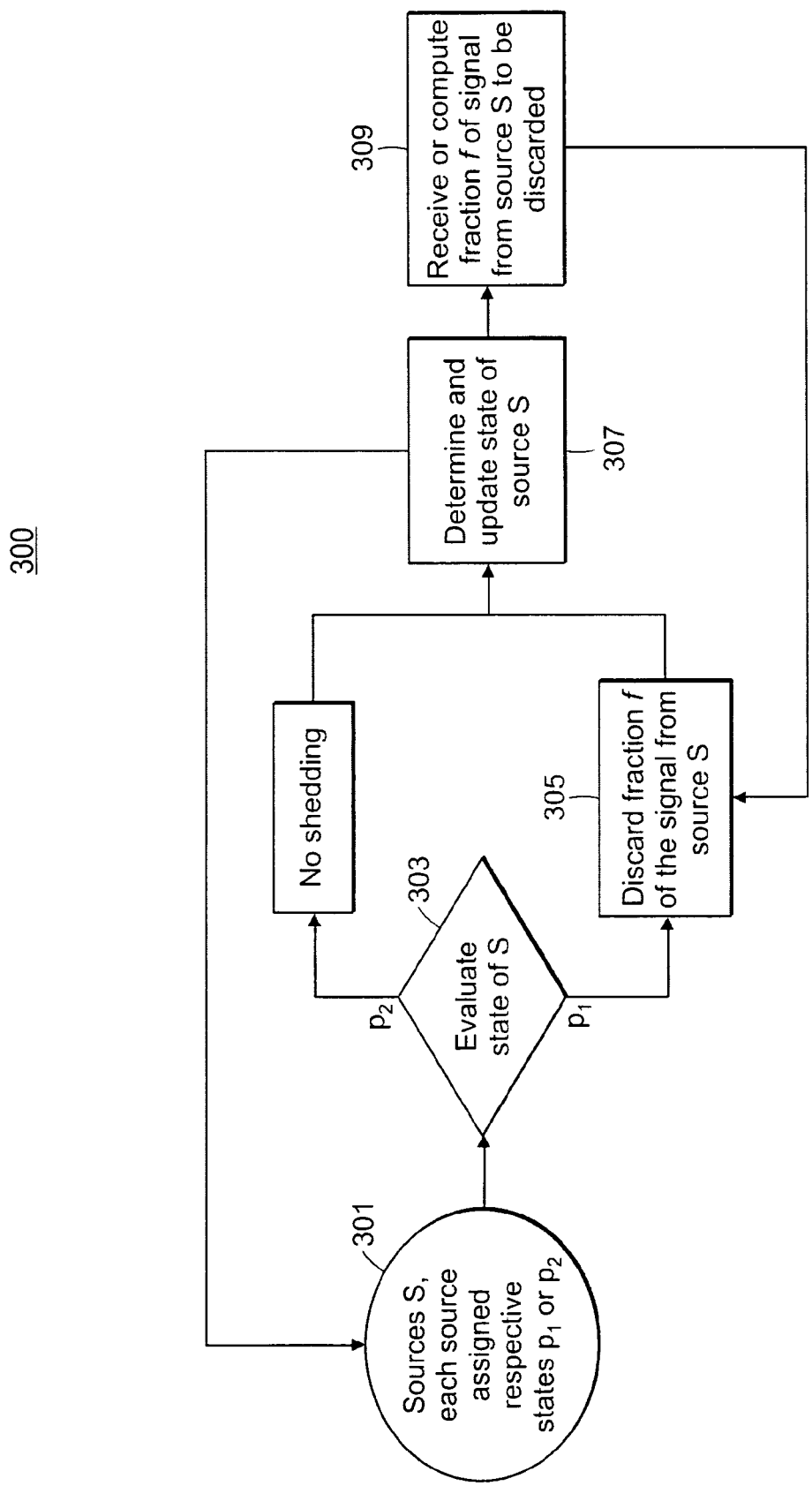
FIG. 3 is a flow diagram of one embodiment of the method.

The first time the method 300 shown in FIG. 3 is applied, no load-shedding is performed (steps 303 and 305 are omitted). This allows for the determination and assignment of states $p_1$ and $p_2$ to all sources S and inputting and calculation of fraction f of the signal to be discarded from each respective source S. The description below assumes that the state of each source has been determined and assigned and all fractions f are known.

At step 301, signal from each source S is collected and passed to means for analysis such as analysis and archiving platform 108 (FIG. 1).

At step 303, the state of the source S is evaluated. If the state of source S is not $p_1$, then no load-shedding is performed and control is passed to step 307. If the state of source S is $p_1$, then pre-determined fraction f of the signal from source S is discarded at step 305. If, for example, source S is a patient data collecting device and the patient's state is "normal", then shedding step 305 is performed. If, however, the patient's state is not "normal", i.e., is "pathologic", then step 305 is omitted.

Fraction f can be measured in any suitable manner. For example, if the signal stream from source S comprises packets, then fraction f can specify what percent of the packets is to be discarded. Alternatively, fraction f can be inputted or computed as a fraction of the threshold duration T employed by step 220 (smoothing) and described above with reference to FIG. 2. For example, if threshold duration T is 5 minutes and f=0.25, then 1.25 minutes will be discarded out of every 5 minutes of a signal. Similarly, in the embodiment where the method of FIG. 3 is employed by an atrial fibrillation monitoring system, threshold duration T can be measured in heart beats. In this embodiment, if T=300 beats and f=0.25, then 75 beats will be discarded out of every 300.

At step 307, based on the signal from each source S, this source's state is determined and updated. In the atrial fibrillation monitoring system, any of the atrial fibrillation detection methods described above may be used for the purpose of determining whether source S was in a "normal" or a "pathologic" state. The means for determining the state of source S (such as analysis and archiving system 108 in FIG. 1) then assigns the value of the state to its respective source and uses this value in the next comparison performed in step 303.

In step 309, fraction f is inputted or computed as described above. The means for receiving and computing fraction f (such as analysis and archiving system 108 in FIG. 1) then updates the value of f used in the next shedding of the signal from source S performed in step 305.

It some embodiments, each source S may be assigned its respective fraction f. For example, individual patients may vary in manifesting the symptoms of a pathologic condition. Accordingly, it may be desirable to discard a different fraction of the signals collected from different patients.

In other embodiments, a state of a source may take more than two values. For example, a patient may be in states such as "normal", "mild pathology" or "severe pathology". In this embodiment, it may be desirable to discard different fractions of a signal from a given patient, depending on the state that this patient is in. Accordingly, each state of a given source S may be assigned its own respective fraction f.

It is to be understood that, depending on a specific embodiment, step 309 can be performed before or simultaneously with steps 301 and 303. For example, if the same value of fraction f is used for all sources S and for all states of each source, then step 309 may be performed once, during the initializing run of method 300 of FIG. 3, and the relative order in which step 309 is performed is left to the discretion of those performing the method.

Following updating the states of each source S and fraction or fractions f, method 300 is applied again, beginning with step 301.

In another embodiment, the monitoring system disclosed herein collects signals from a plurality of sources $S_i$ selected from a set of sources $\{S_1, S_2, \ldots\}$. Each source $S_i$ has state $p_{i,k}$ assigned to it. Each state is selected from a set of states $\{p_{1,1}, p_{1,2}, \ldots, p_{1,N}; p_{2,1}, p_{2,2}, \ldots, p_{2,N}; \ldots\}$. Here, i denotes the ordinal number of a source and is an integer greater than one; N denotes the total number of states per each source and is an integer not less than two; and k denotes the ordinal number of a state of the i-th source and is an integer from 1 to N.

The load-shedding method implemented in such a system performs the steps of: obtaining (by receiving as an input or computing) fractions $f_{i,k}$, determining respective state $p_{i,k}$ of signal source $S_i$ based on the signal from source $S_i$; and, for each source signal $S_i$ in state $p_{i,k}$, discarding fraction $f_{i,k}$ of a signal from source $S_i$. Here, each $0 \leq f_{i,k} < 1$ is a fraction of a signal from source $S_i$ to be discarded if source $S_i$ is in state $p_{i,k}$.

In one embodiment, state $p_{i,k}$ is selected from a set of states $\{p_{i,1}, p_{i,2}\}$; fraction $f_{i,1}$ is 0; and fraction $f_{i,2}$ is a fraction greater than zero and less than 1. Preferably, $f_{i,2}$ is a fraction greater than zero and less than or equal to about 0.5.

In some embodiments, each source $S_i$ is a physiological data collecting device. For example, the signal can be an electrocardiogram signal. In such an embodiment, state $p_{i,1}$ can correspond to normal heart activity and state $p_{i,2}$ can correspond to atrial fibrillation.

In some embodiments, each source $S_i$ is assigned state $p_{i,k}$ if said state $p_{i,k}$ has a duration above threshold duration $T_{i,k}$. (See description of smoothing at step 220, FIG. 2, above.) In these embodiments, fractions $f_{i,k}$ are computed as fractions of threshold $T_{i,k}$. For example, fraction $f_{i,k}$ can be less than or equal to about 50% of $T_{i,k}$ or less than or equal to about 25% of $T_{i,k}$.

As mentioned above, $T_{i,k}$ can be measured in units of time or (in the embodiments, where the signal is an electrocardiogram signal) in numbers of heart beats. Accordingly, in some embodiments, $T_{i,k}$ is less than about 15 minutes, less than about 10 minutes, or, preferably, about 5 minutes or less. Alternatively, $T_{i,k}$ can be about 500 heart beats, about 400 heart beats or, preferably, about 300 heart beats.

IV. Computer-Implemented System

Figure 4:
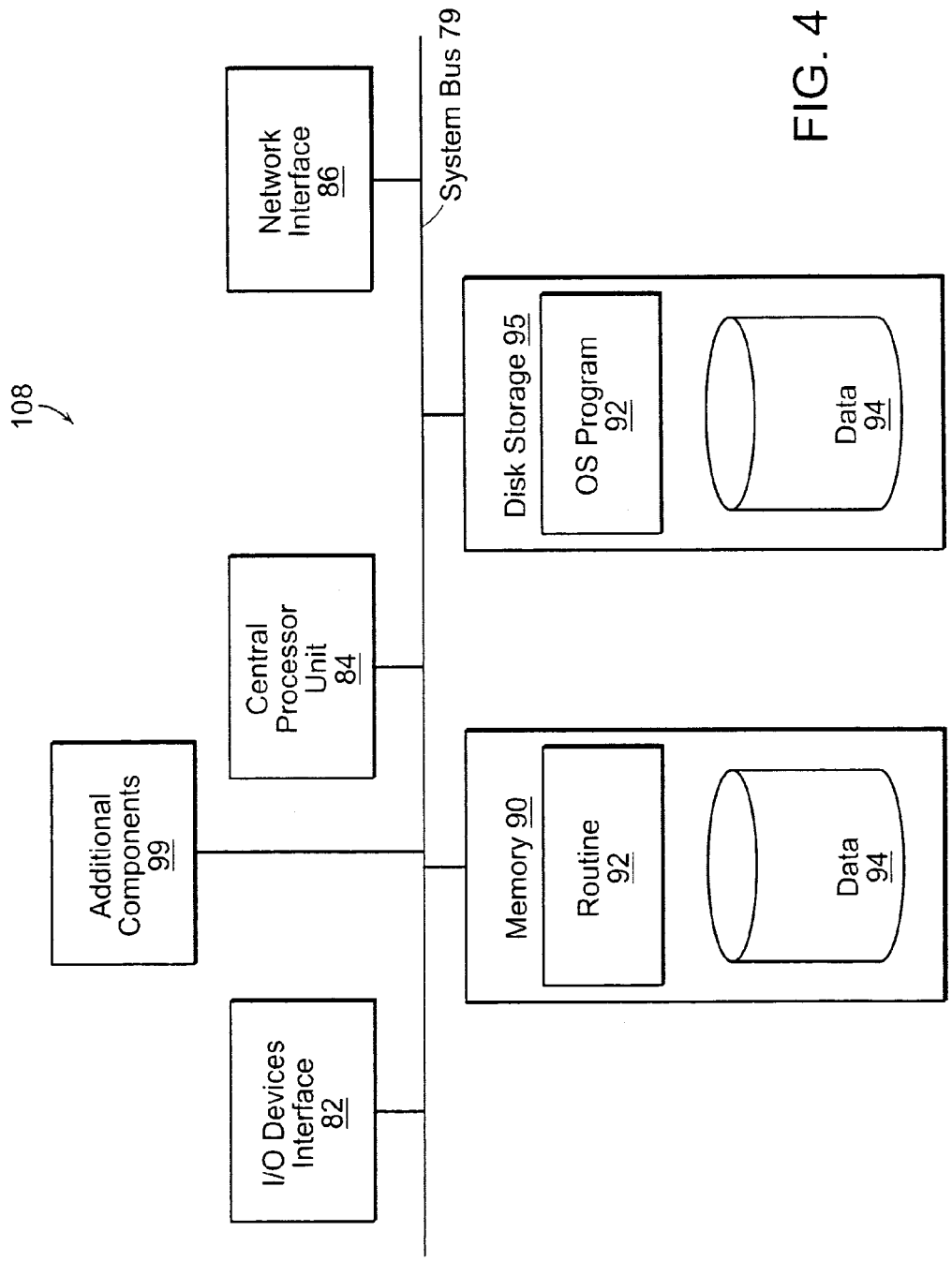
FIG. 4 is a schematic diagram of a computer-implemented system for executing an embodiment of the method.

FIG. 4 is a diagram of the internal structure of a portion of analysis and archiving platform 108 (FIG. 1) that can execute the load-shedding method 300 in cooperation with Afib detection and analysis method such as method 200 described above (FIG. 2). Each component of the system depicted in FIG. 4 is connected to system bus 79, where a bus is a set of hardware lines used for data transfer among the components of a computer or processing system. Also connected to bus 79 are additional components 99 of platform 108 such as additional memory storage, digital processors, network adapters and I/O device. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to remote analysis and archiving platform 108. Network interface 86 allows the computer to connect to various other devices attached to a network (e.g., networks connections 106 and 110 of FIG. 1). Memory 90 provides volatile storage for computer software instructions 92 and data 94 used to implement methods employed by the system disclosed herein (e.g., the Afib analysis method 200 in FIG. 2 and the load-shedding method 300 in FIG. 3). Disk storage 95 provides non-volatile storage for computer software instructions 92 and data 94 used to implement an embodiment of method of the present disclosure. Central processor unit 84 is also attached to system bus 79 and provides for the execution of computer instructions.

In one embodiment, the processor routines 92 and data 94 (e.g., the Afib analysis method 200 in FIG. 2 and the load-shedding method 300 in FIG. 3) are a computer program product, including a computer readable medium (e.g., a removable storage medium such as one or more DVD-ROM's, CD-ROM's, diskettes, tapes, etc.) that provides at least a portion of the software instructions for the system.

Computer program product that combines routines 92 and data 94 may be installed by any suitable software installation procedure, as is well known in the art. In another embodiment, at least a portion of the software instructions may also be downloaded over a cable, communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the routines/program 92 disclosed herein.

In alternate embodiments, the propagated signal is an analog carrier wave or a digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that analysis and archiving platform 108 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and/or the like.

Equivalents

While this invention has been particularly shown and described with references to particular embodiments thereof, it will be understood by those skilled in the art that various changes in form and details may be made therein without departing from the scope of the invention encompassed by the appended claims.

What is claimed is:

1. A method of load-shedding in a computer network system having a plurality of signal sources, said method comprising:
    a. for each signal source $S_i$ selected from a set of sources $\{S_1, S_2, \ldots\}$, each source having state $p_{i,k}$ selected from a set of states $\{p_{1,1}, p_{1,2}, \ldots, p_{1,N}; p_{2,1}, p_{2,2}, \ldots, p_{2,N}; \ldots\}$, wherein i is an integer greater than one, N is an integer not less than two and k is an integer from 1 to N:
        i. obtaining by receiving as an input or by computing fractions $f_{i,k}$, wherein each $0 \leq f_{i,k} < 1$ is a fraction of a signal from source $S_i$ to be discarded if source $S_i$ is in state $p_{i,k}$; and
        ii. determining respective state $p_{i,k}$ of signal source $S_i$ based on the signal from source $S_i$; and
    b. for each source signal $S_i$ in determined state $p_{i,k}$, discarding fraction $f_{i,k}$ of a signal from source, wherein a device in the computer network system is configured to transmit an undiscarded portion of the signal from source $S_i$, to a processing and storage device.

2. The method of claim 1, wherein
   state $p_{i,k}$ is selected from a set of states $\{p_{i,1}, p_{i,2}\}$;
   fraction $f_{i,1}$ is 0; and
   fraction $f_{i,2}$ is a fraction greater than zero and less than 1.

3. The method of claim 2 wherein $f_{i,2}$ is a fraction greater than zero and less than or equal to about 0.5.

4. The method of claim 2, wherein each source $S_i$ is a physiological data collecting device.

5. The method of claim 4, wherein the signal is an electrocardiogram signal.

6. The method of claim 5, wherein state $p_{i,1}$ corresponds to normal heart activity and state $p_{i,2}$ corresponds to atrial fibrillation.

7. The method of claim 1, wherein each source $S_i$ is assigned state $p_{i,k}$ if said state $p_{i,k}$ has a duration above a threshold duration $T_{i,k}$.

8. The method of claim 7, wherein fractions $f_{i,k}$ are computed as fractions of threshold $T_{i,k}$.

9. The method of claim 8, wherein $f_{i,k}$ is less than or equal to about 50% of $T_{i,k}$.

10. The method of claim 8, wherein $f_{i,k}$ is less than or equal to about 25% of $T_{i,k}$.

11. The method of claim 7, wherein $T_{i,k}$ is less than or equal to about 15 minutes.

12. The method of claim 7, wherein $T_{i,k}$ is less than or equal to about 10 minutes.

13. The method of claim 7, wherein $T_{i,k}$ is less than or equal to about 5 minutes.

14. The method of claim 7, wherein the signal is an electrocardiogram signal.

15. The method of claim 14 wherein $T_{i,k}$ is about 500 heart beats.

16. The method of claim 14 wherein $T_{i,k}$ is about 400 heart beats.

17. The method of claim 14 wherein $T_{i,k}$ is about 300 heart beats.

18. A method of load-shedding in a computer network system for continuously monitoring one or more patients, said method comprising:
    a. for each patient having a state selected from a "normal" state or a "pathologic" state:
        i. obtaining by receiving as an input or by computing fractions f, wherein $0 \leq f < 1$ and f is a fraction of a signal from each patient to be discarded if said patient is in the "normal" state; and
        ii. determining a respective state of the patient based on a signal from said patient;
    b. for each patient in the "normal" state discarding fraction f of the signal from said patient, wherein a device in the computer network system is configured to transmit an undiscarded portion of the signal from source $S_i$, to a processing and storage device.

19. A computer system for shedding signal load in a network having a plurality of devices, said system comprising:
    a. means for collecting signals from signal sources $S_i$, selected from a set of sources $\{S_1, S_2, \ldots\}$, each source having state $p_{i,k}$ selected from a set of states $\{p_{1,1}, p_{1,2}, \ldots, p_{1,N}; p_{2,1}, p_{2,2}, \ldots, p_{2,N}; \ldots\}$, wherein i is an integer greater than one, N is an integer not less than two and k is an integer from 1 to N;
    b. means for receiving as an input or computing fractions $f_{i,k}$, wherein each $0 \leq f_{i,k} < 1$ is a fraction of a signal from source $S_i$ to be discarded if source $S_i$ is in state $p_{i,k}$;
    c. means for determining respective state $p_{i,k}$ of each signal source $S_i$; and
    d. means for discarding fraction $f_{i,k}$ of a signal from source $S_i$ for each source signal $S_i$ in determined state $p_{i,k}$, wherein a device in the computer network system is configured to transmit an undiscarded portion of the signal from source $S_i$, to a processing and storage device.

20. The computer system of claim 19, wherein
state $p_{i,k}$ is selected from a set of states $\{p_{i,1}, p_{i,2}\}$;
fraction $f_{i,1}$ is 0;
fraction $f_{i,2}$ is a fraction greater than zero and less than 1;
the signal is an electrocardiogram signal; and
state $p_{i,1}$ corresponds to normal heart activity and state $p_{i,2}$ corresponds to atrial fibrillation.

21. The computer system of claim 19, wherein each source $S_i$ is assigned state $p_{i,k}$ if said state $p_{i,k}$ has a duration above threshold duration $T_{i,k}$.

22. The computer system of claim 21, wherein fractions $f_{i,k}$ are computed as fractions of threshold $T_{i,k}$.

23. The computer system of claim 21, wherein $T_{i,k}$ is less than or equal to about 15 minutes.

24. The computer system of claim 21, wherein the signal is an electrocardiogram signal, and $T_{i,k}$ is between about 500 and 300 heart beats.

25. A computer system for signal load-shedding in a system for continuously monitoring one or more patients, said system comprising:
 a. means for collecting signals from each patient having respective state selected from a "normal" state and "pathologic" state;
 b. means for receiving as an input or computing fractions f, wherein each $0 \leq f < 1$ is a fraction of a signal from each patient to be discarded if said patient is in the "normal" state;
 c. means for determining respective state of each patient based on a signal from each patient;
 d. means for discarding fraction f of the signal from each patient in the "normal" state; and
 e. means for transmitting an undiscarded portion of the signal from each patient to a processing and storage device.

* * * * *